United States Patent [19]

Andriollo et al.

[11] Patent Number: 5,401,709
[45] Date of Patent: Mar. 28, 1995

[54] ANTIBIOTIC AB-041 DERIVED FROM STREPTOMYCES SP. NCIMB 40428, HERBICIDAL COMPOSITIONS, AND METHODS OF USE

[75] Inventors: Nunzio Andriollo, Bollate; Alessandro Scacchi, Novara; Giorgio E. Borgonovi, Milan; Giorgio Cassani, Arluno; Silvia Spera, Novara; Gianfranco Guglielmetti, Bogogno; Giorgio Pirali, Saronno; Giovanni Confalonieri, Monza, all of Italy

[73] Assignee: Ministero Dell 'Universita' E Della Ricerca Scientifica E Tecnologica, Rome, Italy

[21] Appl. No.: 983,744

[22] Filed: Dec. 1, 1992

[30] Foreign Application Priority Data

Dec. 4, 1991 [IT] Italy .................... MI91A3254

[51] Int. Cl.⁶ .................... A01N 63/02; A61K 35/70
[52] U.S. Cl. .................... 504/117; 424/117; 424/93.43; 435/130; 435/253.5
[58] Field of Search ............ 424/117, 93 G; 504/117; 435/130, 253.5; A01N 63/02

[56] References Cited

U.S. PATENT DOCUMENTS

| | | | |
|---|---|---|---|
| 3,629,405 | 12/1971 | Hamill et al. | 424/117 |
| 3,869,277 | 3/1975 | Berger et al. | 504/320 |
| 4,552,584 | 11/1985 | Takematsu et al. | 504/117 |
| 4,584,009 | 4/1986 | Adachi et al. | 504/117 |
| 5,126,265 | 6/1992 | Cidaria et al. | 435/253.5 |

FOREIGN PATENT DOCUMENTS

0371509A2 6/1990 European Pat. Off. .

OTHER PUBLICATIONS

Arai, et al "Herbicidins A and B, Two New Antibiotics with Herbicidal Activity", *J. Antibiotics* 29(9): 863–875. 1976.

Primary Examiner—Peter O'Sullivan
Assistant Examiner—S. Mark Clardy
Attorney, Agent, or Firm—Oblon, Spivak, McClelland, Maier & Neustadt

[57] ABSTRACT

The antibiotic AB-041 is described, obtained by controlled aerobic cultivation of Streptomyces sp. NCIMB 40428 in an aqueous culture medium. The antibiotic AB-041 exhibits biological activity, and in particular herbicidal activity.

19 Claims, 6 Drawing Sheets

Fig. 4
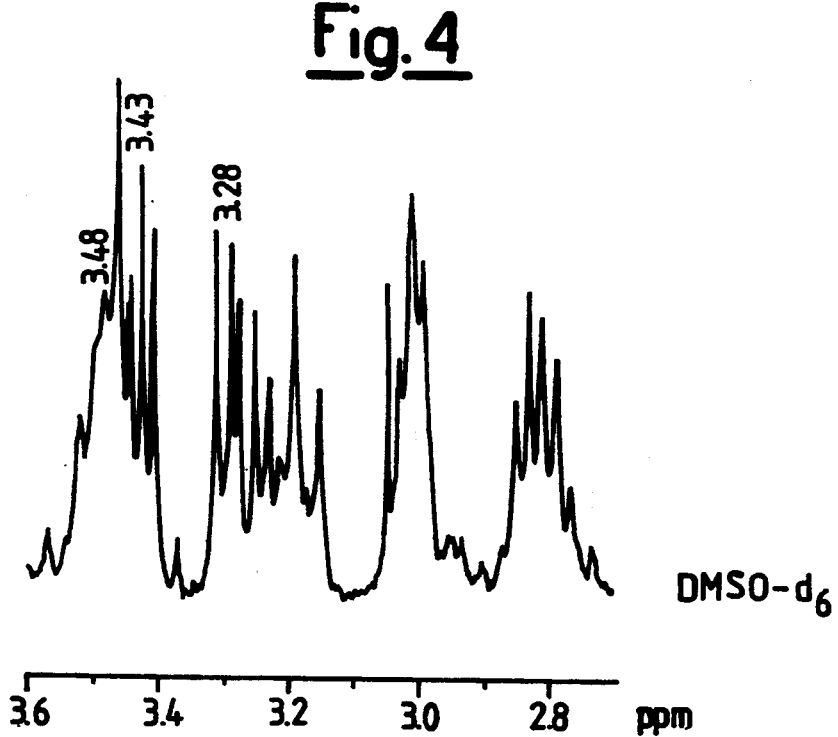
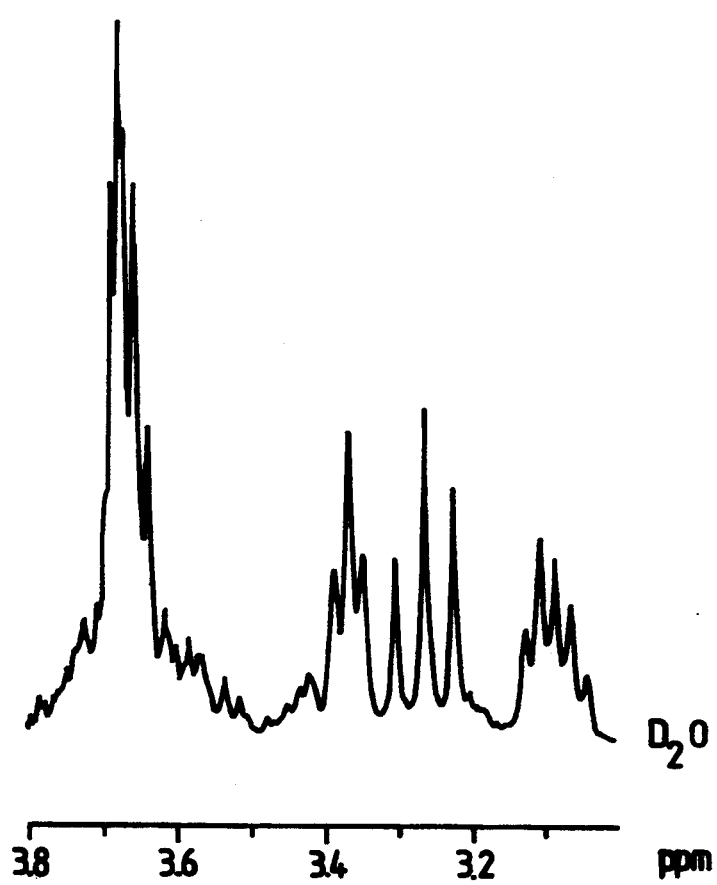

ANTIBIOTIC AB-041 DERIVED FROM *STREPTOMYCES SP.* NCIMB 40428, HERBICIDAL COMPOSITIONS, AND METHODS OF USE

This invention relates to antibiotic substances arbitrarily named AB-041.

It also relates to the process for their production by fermenting Streptomyces sp. NCIMB 40428 and their use in the protection of crops from infesting grasses sensitive to them.

The high herbicidal activity shown by said substances makes them suitable for agricultural use in protecting useful crops against infesting plants.

This activity is exhibited towards a wide range of infesting plants, whereas the absence of toxic effects on useful plants has been demonstrated.

The present invention provides a mixture, known as antibiotic AB-041 obtained by fermenting Streptomyces sp. NCIMB comprising all the components with herbicidal activity.

It should be noted that the present invention is not limited to the use of Streptomyces sp. NCIMB 40428 but also comprises the use of natural or artificial mutants or variants of said microorganism, provided they produce the antibiotic AB-041.

BRIEF DESCRIPTION OF THE DRAWINGS

The figures show UV, IR, and NMR spectra for antibiotic AB-041.

FIG. 4 shows the $^1H$NMR spectrum in DMSO-d6.

Said antibiotic has shown the following properties:

Physical and chemical properties of the antibiotic AB-041

The antibiotic AB-041 is in the form of a white or white-ochre powder characterised by:

a) good solubility in water, in dimethylsulphoxide and dimethylsulphoxide/water mixtures, but practically insoluble in ethyl ether and hexane.

b) contains carbon, hydrogen, nitrogen, oxygen, sulphur.

c) molecular weight 463.1373, determined by FAB-HRMS spectra which show peaks at m/z=464.1452±0.0006 (MH)+ and m/z=486.1270±0.0007 (MNa)+ under the following operating conditions: HRFAB-MS, Xe at 9.5 kV: glycerol matrix.

Figure 1:
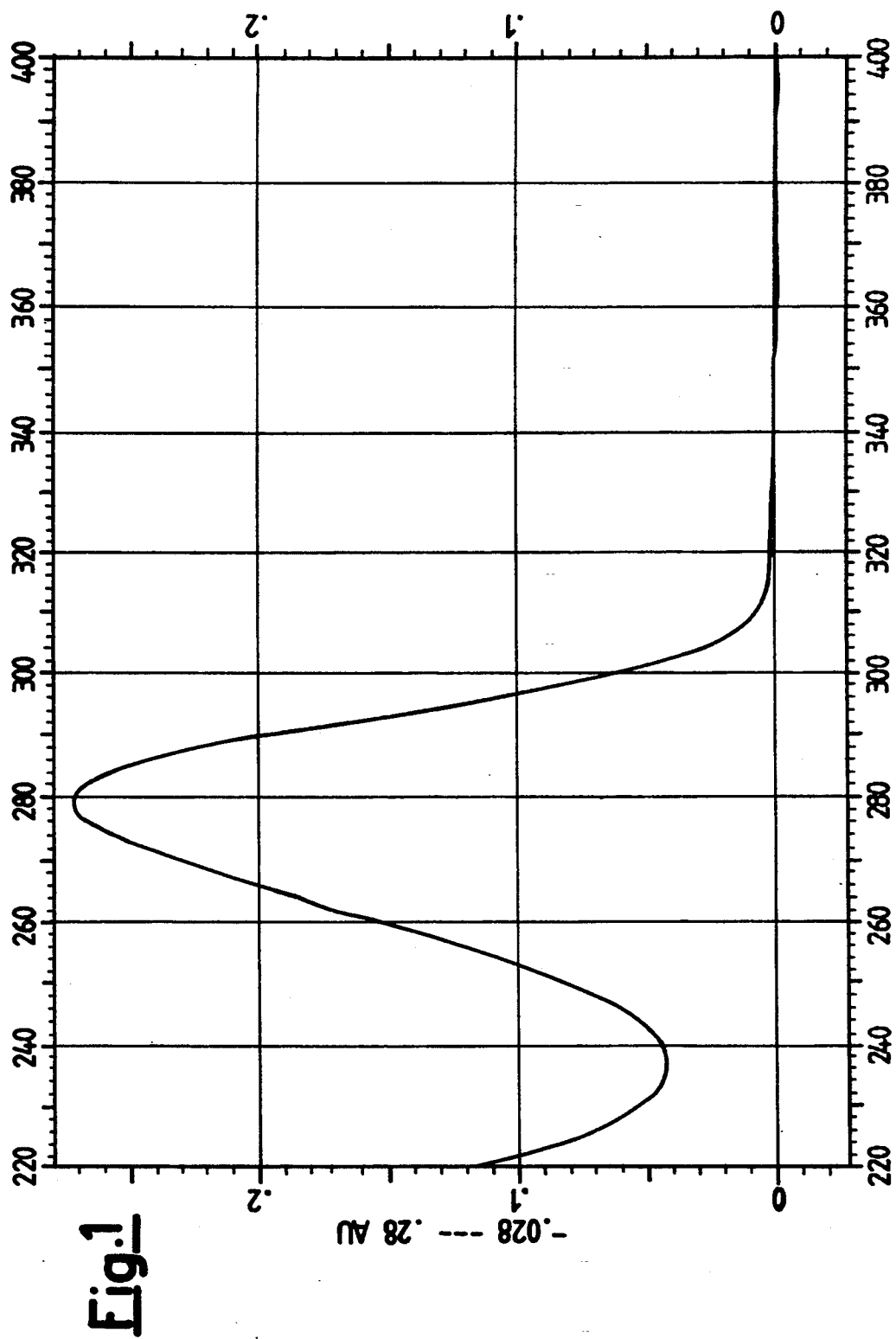
FIG. 1 shows the UV absorption spectrum in water (pH 4.5).
Figure 2:
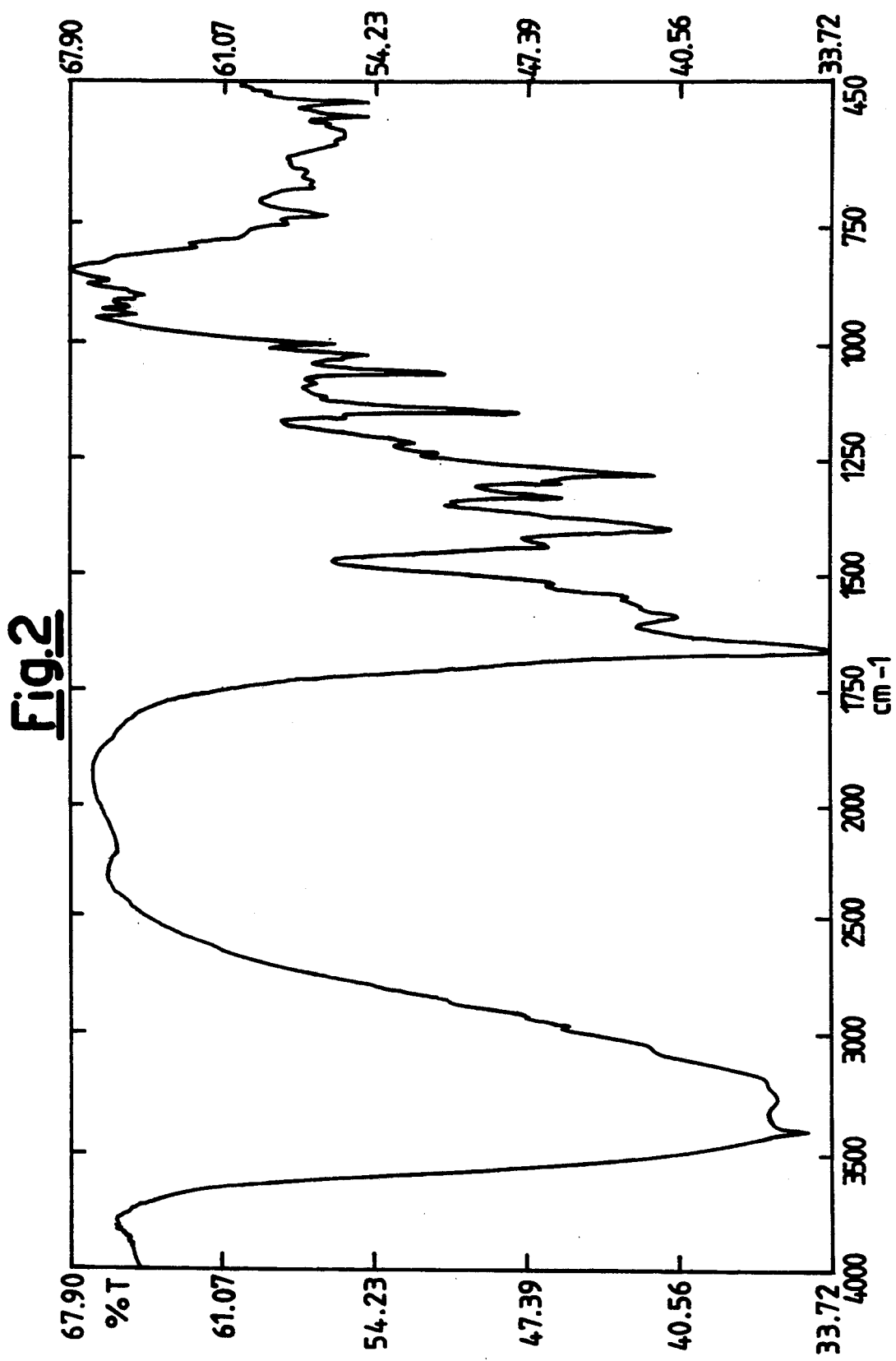
FIG. 2 shows the IR absorption spectrum in KBr pastille.
Figure 3:
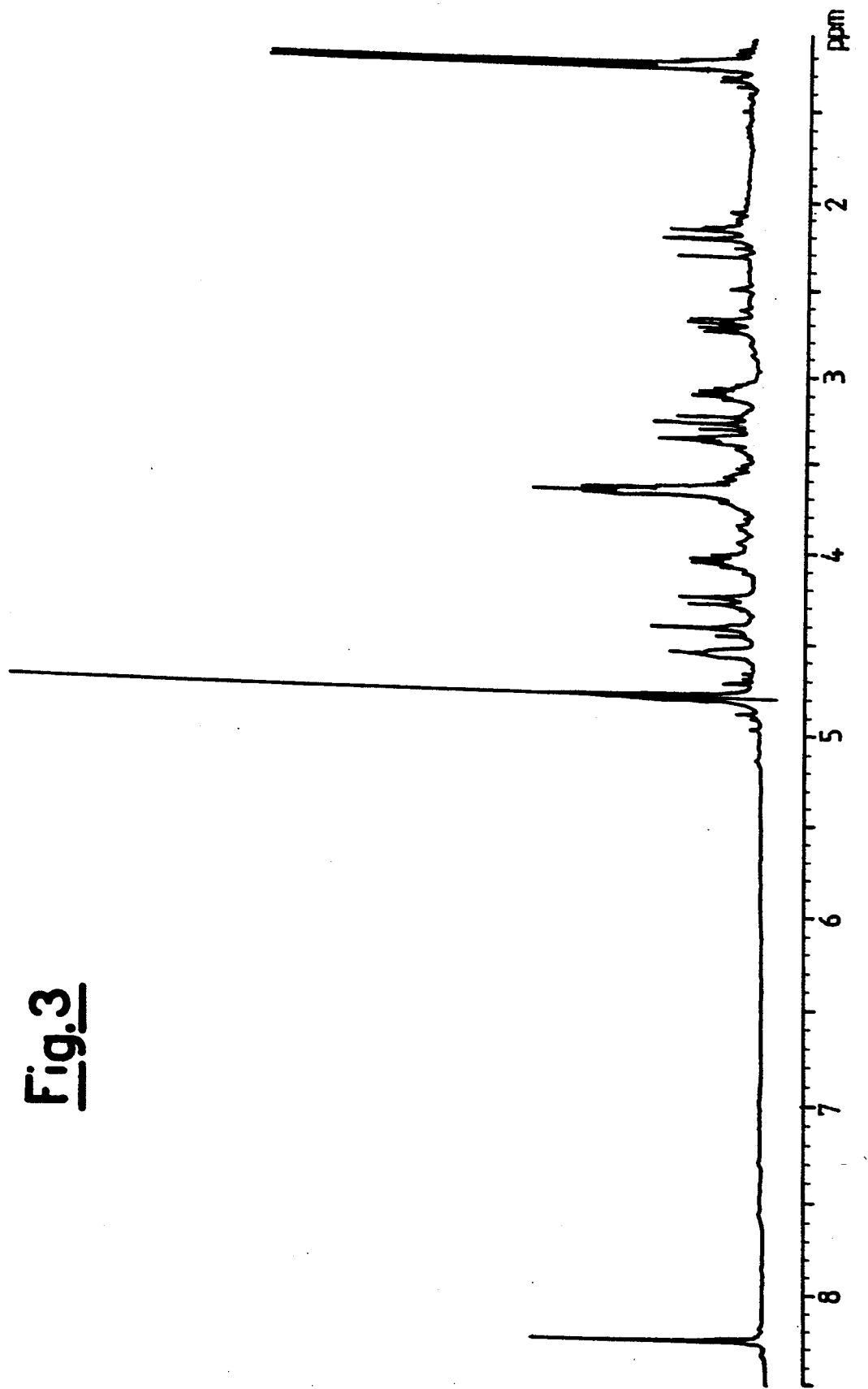
FIG. 3 shows the $^1H$NMR spectrum in $D_2O$.

The value of [M H]+ at m/z 464 was confirmed by the spectra obtained in high-performance liquid chromatography/thermospray mass spectrometry (HPLC/TSMS) with mobile phase consisting of a 0.05M solution of ammonium acetate and methanol (50/50).

e) empirical formula: $C_{16}H_{25}N_5O_9S$ ultraviolet (UV) absorption spectrum recorded in water at pH 4.5 shown in FIG. 1 of the accompanying drawings. It shows an absorption maximum at 278 nm.

f) infrared (IR) absorption spectrum in KBr pastille shown in FIG. 2 of the accompanying drawings, with the following maxima: 3395; 1663; 1594; 1449; 1403; 1338; 1307; 1285; 1246; 1225; 1159; 1102; 1074; 1037; 1017; 960; 942; 917; 888; 741 cm$^{-1}$.

g) $^1H$NMR spectrum shown in FIG. 3 of the accompanying drawings.

The spectrum was recorded in $D_2O$ on a Bruker AM 300 NMR spectrometer. 3000 scans were made with a delay of 2 sec. between each scan.

The chemical shifts were indirectly referred to TMS=0.00 ppm ($\delta$ TMS) assuming as internal reference the deuterated water peak at 4.80 ppm. The three superposed signals at 3.67 ppm were resolved by comparing the spectrum in $D_2$ with the analogous spectrum recorded in hexadeuterodimethylsulphoxide (DMSO-d6) in which the corresponding signals appear distinct at 3.48, 3.43 and 3.28 ppm (FIG. 4) and by two-dimensional NMR experiments.

Figure 5:
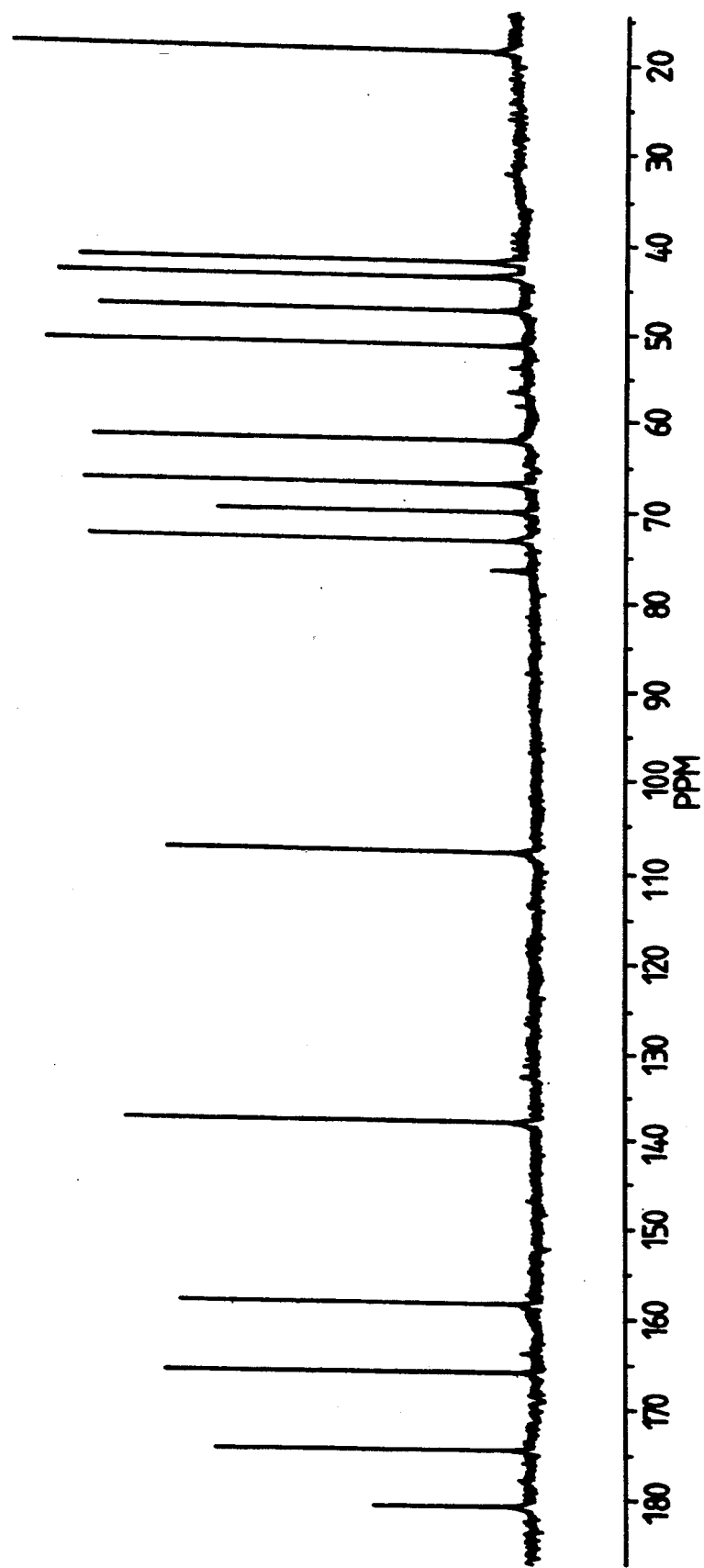
FIG. 5 shows the $^{13}C$ NMR spectrum in $D_2$.
Figure 6:
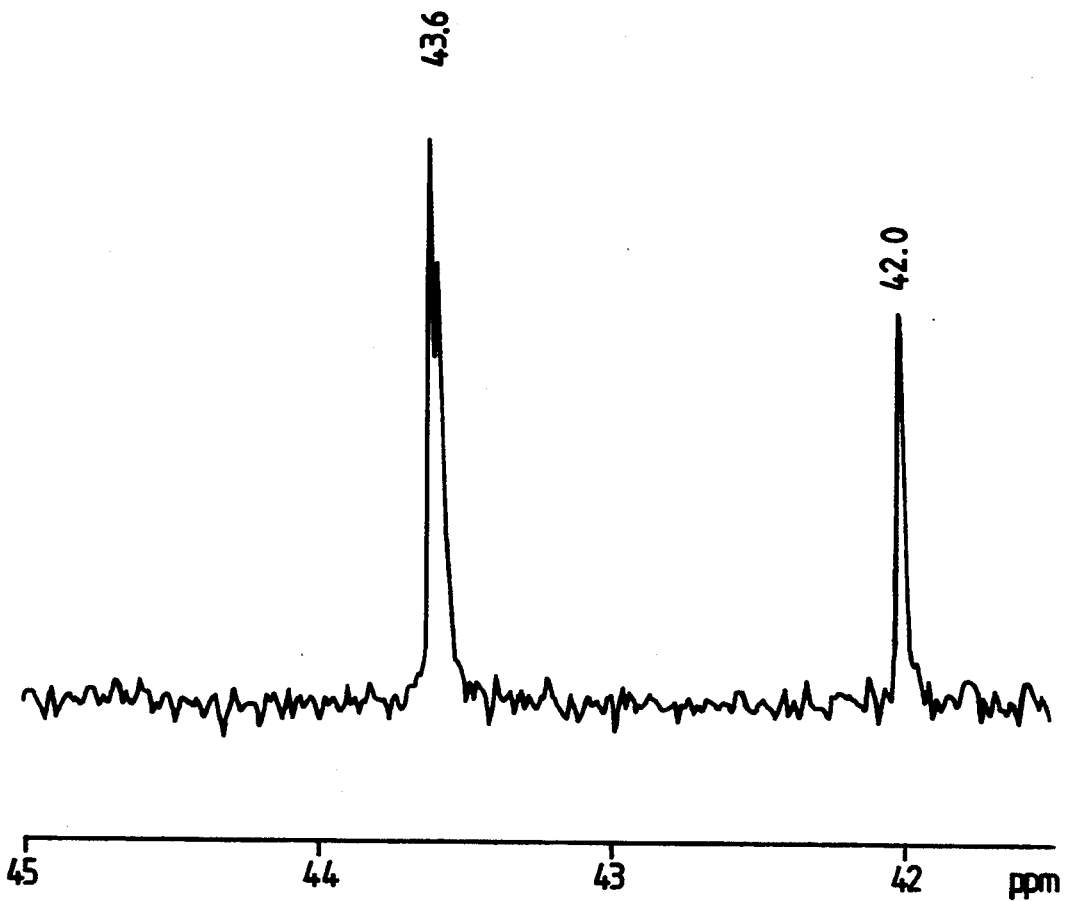
FIG. 6 shows the superimposing of two signals at 43.6 ppm.

$\delta$(ppm): 8.26 (s, 1H); 4.55 (t, 1H); 4,43 (d, 1H); 4.26 (d, 1H); 4.04 (m, 1H); 3.67 (m, 3H); 3.36 (t, 1H); 3.26 (t, 1H); 3.09 (m, 1H); 2.71 (dd, 1H); 2.19 (d, 1H); 1.26 (d, 3H). h) $^{13}C$ NMR spectrum shown in FIG. 5 recorded in $D_2O$ on a Bruker AM 300 spectrometer. 10000 scans were made with a delay of 20 sec. between each scan (90° pulse). The chemical shifts were indirectly referred to TMS=0.00 ppm ($\delta$ TMS). The enlargement of FIG. 6 shows the superimposing of the two signals at 43.6 ppm. The data relative to the multeplicity of signals were obtained by DEPT experiments at 45°, 90° and 135°.

$\delta$(ppm): 180.9 (s): 174.7 (s) 165.8 (s); 158.3 (s); 137.8 (d); 107.8 (s); 73.1 (d); 70.0 (s) 66.8 (t); 62.0 (t); 51.1 (d); 47.3 43.6 (t) (t); 43.6 (d);43.6 (t); 42.0 (d) 18.5 (q).

i) retention time (Rt) of about 4.7 min. when analyzed in a reverse phase HPLC column under the following conditions:

Column=Hibar LiChrospher 100 RP 18 encapped (5 μm) 250 ×4 mm (Merck, Darmstadt; Germany)

Precolumn=LiChroCART 4—4, LiChrospher 100 RP 18 encapped (5 μm) (Merck, Darmstadt; Germany)

Eluent=methanol:potassium phosphate monobasic 20 mM in water adjusted to pH=3.5 with phosphoric acid (12.1:87.9 v/v)

Flow=0.7 ml/min

Temperature=40° C.

UV detector 276 nm l) positive colorimetric reaction with ninhydrin in acetone 0.2% (w/v); with pinacryptol yellow in water (0.07% w/v); negative colorimetric reaction with diazotation reagent and coupling with α-naphthol.

m) Rf=0.35 cellulose P chromatography plate (Merck AG,Darmstadt, Germany) with acetonitrile/water 91:9 (v/v) as eluent.

Morphology and culture characteristics of Streptomyces sp. NCIMB 40428

The micro-organism was isolated from an earth sample taken at San Martino in Colle (Perugia) and catalogued with the internal coding SD749.

A culture of this micro-organism was filed on Jun. 27, 1991 in accordance with the treaty of Budapest at the National Collection of Industrial and Marine Bacteria Ltd., 23 St. Machar Drive, Aberdeen AB2 1RY, Scotland, U.K., where it was granted the access number NCIMB 40428. The morphological characteristics are given in Table A (the culture names are those used by the International Streptomyces Program).

TABLE A

| ISP code | Culture medium | Description |
|---|---|---|
| M1 | Tryptone yeast broth | Discrete growth, formation of melanin pigment |
| M2 | Malt extract agar | Abundant growth, low colonies, white aerial mycelium, slight melanin pigment |
| M3 | Oat meal agar | Abundant growth, high colonies, grey hygroscopic aerial mycelium |
| M4 | Starch agar | Abundant growth, low colonies, white aerial mycelium |
| M5 | Glycerol asparagine agar | Low growth, low colonies, aerial mycelium absent |
| M6 | Peptone iron agar | Discrete growth, low colonies, grey aerial mycelium |
| M7 | Tyrosine agar | Low growth, low colonies, aerial mycelium absent |
| — | Nutrient agar | Abundant growth, low colonies, clear |
| — | Emerson agar | Abundant growth, high radial colonies, abundant white aerial mycelium |
| — | V8 tomato juice agar | Abundant growth, low colonies, abundant grey aerial mycelium |
| — | Dextrose potato | Abundant growth, low colonies, white aerial mycelium, slight melanin pigment. |

Table B reports some characteristics of this strain.

TABLE B

| CHARACTERISTIC | RESPONSE |
|---|---|
| Resistance to NaCl (7%) | Negative |
| Resistance to phenol (0.1%) | Positive |
| Growth at 45 degrees centigrade | Negative |
| Growth at 4 degrees centigrade | Negative |
| Lipolysis | Positive |
| DNA-ase | Negative |
| Hydrogen sulphide production | Negative |
| Antibiosis towards: | |
| B. subtilis NCIMB 3610 | Negative |
| M. luteus NCIMB 196 | Negative |
| C. albicans CBS 562 | Negative |
| S. cerevisiae CBS 1171 | Weak |
| S. murinus ISP 5091 | Negative |
| A. niger LIV 131 | Negative |

Table C indicates the growth of the strain on some organic substances, as sole carbon source.

TABLE C

| COMPOUND | GROWTH |
|---|---|
| N-acetyl-D-glucosamine | +++ |
| Adonitol | +++ |
| L-arabinose | +++ |
| Cellobiose | +++ |
| Galactose | +++ |
| Glycerol | +++ |
| Glucose | +++ |
| Inositol | + |
| Lactose | ++ |
| 2-keto-D-gluconate | +++ |
| Maltose | ++ |
| Melezitose | ++ |
| Methyl-D-glucoside | ++ |
| Raffinose | ++ |
| Saccharose | +++ |
| Sorbitol | +++ |
| Threalose | ++ |
| Xylitol | +++ |
| Xylose | +++ |

Table D indicates the sensitivity of the strain to certain antibiotics.

TABLE D

| ANTIBIOTIC | DOSE (micrograms) | SENSITIVITY |
|---|---|---|
| Nalidixic acid | 30 | — |
| Ampicillin | 10 | ++ |
| Bacitracin | 10(1) | +++ |
| Cephaloridine | 30 | +++ |
| Chloramphenicol | 30 | + |
| Chlortetracycline | 30 | +++ |
| Erythromycin | 15 | ++ |
| Phosphomycin | 50 | ++ |
| Gentamycin | 10 | +++ |
| Kanamycin | 30 | +++ |
| Lincomycin | 2 | — |
| Neomycin | 30 | +++ |
| Novobiocin | 30 | +++ |
| Oleandomycin | 15 | + |
| Oxytetracycline | 30 | +++ |
| Penicillin | 10(1) | + |
| Polymyxin B | 300(1) | ++ |
| Rifamycin | 30 | ++ |
| Rifampicin | 30 | ++ |
| Streptomycin | 10 | +++ |
| Tetracycline | 30 | +++ |
| Tobramycin | 10 | +++ |
| Vancomycin | 30 | +++ |

(1)International units
+ Indication of positive growth
— Indication of lack of growth As in the case of other micro-organisms, Streptomyces sp, NCIMB 40428 can undergo variations.

For example, artificial variants or mutants can be obtained by treatment with various known mutagens such as X-rays or ultraviolet rays (UV), high frequency waves and chemical substances such as nitrous acid, halogenated alkylamines, nitrosoguanidine, camphor and the like.

All those natural or artificial variants or mutants pertaining to the Streptomyces species which produce the antibiotic AB-041 are considered equivalent to the Streptomyces sp. NCIMB 40428 strain and are included within the scope of the present invention.

Production process for the antibiotic AB-041

The process for producing the antibiotic AB-041 consists of cultivating Streptomyces NCIMB 40428 or a mutant equivalent thereof, under controlled aerobic fermentation conditions in an aqueous nutrient, and separating the antibiotic by known means. Culture nutrients or fermentation broths commonly used for producing antibiotics can be used, however certain culture media are preferred.

Said culture media must contain carbon and nitrogen sources which can be assimilated by micro-organisms of the Streptomyces genus, and must also contain low levels of inorganic salts.

They must also contain traces of those metals necessary for microorganism growth and development, which may already be present as impurities in the carbon or protein nitrogen sources provided for the bacterial growth, or if necessary can be added to the culture medium.

Generally, the carbon source used can consist of carbohydrates, in particular saccharides such as glucose or fructose, or alternatively or in addition starches or industrial products chemically similar to starches such as soluble dextrin starch, or polyalcohols such as glycerol.

Said compositions can be used singly or in combination. The concentration of the carbon source in the culture medium generally depends on the type and quantity of other ingredients in the medium, however concentrations between 0.5 and 5% by weight are generally satisfactory.

The nitrogen source used can be protein hydrolyzates such as yeast extract, casein hydrolyzate, or flour such as soya flour, or industrial products marketed for this purpose such a profilo, corn steep liquor, or distillers solubles.

These compounds can be used singly or in combination, in concentrations varying between 0.2 and 6% by weight in the culture medium.

The trace metals present can be for example cobalt, manganese, iron and the like.

The inorganic salts which can be used include for example sodium. potassium, magnesium, ammonium and calcium salts, as phosphates, sulphates, chlorides, carbonates or nitrates.

Certain culture media have demonstrated a particular capacity to stimulate production of the antibiotic AB-041 from Streptomyces sp. NCIMB 40428, such as the following aqueous formulations, which are used in the subsequent preparation examples.

| (ingredients) | CONCENTRATION (g/l) |
|---|---|
| CULTURE MEDIUM P | |
| profilo (cottonseed flour) | 10 |
| glycerol | 15 |
| CaCO$_3$ | 3 |
| CULTURE MEDIUM V | |
| meat extract | 4 |
| yeast extract | 1 |
| peptone | 4 |
| dextrose | 10 |
| NaCl | 2.5 |
| CULTURE MEDIUM V1 | |
| meat extract | 3 |
| peptone | 5 |
| CULTURE MEDIUM S | |
| glucose | 1 |
| meat and liver peptone | 10 |
| meat extract | 5 |
| NaCl | 3 |
| agar | 12.5 |

The strain Streptococcus sp. NCIMB 40428 can be made to grow at temperatures between 20° C. and 35° C., and preferably between 25° C. and 30° C.

The pH conditions can vary from about 5 to about 9.

The sterile air blown into the culture medium is generally used in a quantity such as to maintain an oxygen concentration of 20% of the saturation value or more in the medium except around 24 hours after inoculation, when the oxygen concentration can fall to lower values.

The antibiotic production during the fermentation can be followed by biological activity tests on broth samples.

Fermentation is effected for a time such as to obtain substantial biological activity. A time of 72–120 hours is generally sufficient.

Separation and purification of the antibiotic

After cultivation under the aforedescribed fermentation conditions, the antibiotic AB-041 can be separated from the culture broth and then purified by conventional methods of the separation art.

These methods include for example precipitation with non-solvents, ultrafiltration, reverse osmosis, silica gel chromatography, cellulose chromatography, reverse phase chromatography, ion exchange resin chromatography, chromatography on non-ionic macroporous resins and the like, size exclusion chromatography (SEC), and gel permeation chromography (GPC).

The antibiotic produced during the fermentation is mainly found in the fermentation broth.

A preferred method for recovering the antibiotic AB-041 is to separate the mycelium mass from the culture broth by centrifuging. The broth thus obtained is filtered through a 1 μm filter and ultrafiltered through a spiral membrane with 20 kD nominal exclusion. The permeate is concentrated through a spiral membrane by reverse osmosis with 500 D nominal exclusion.

That retained by the reverse osmosis is treated over non-ionic resin which retains certain lipophilic impurities but does not retain the antibiotic AB-041, and is then fed into a column containing an ion exchange resin (such as AMBERLITE IRA 401 previously converted into the chloride form), the resin is then washed with water and the product is eluted with an aqueous HCl solution.

The fractions containing the antibiotic AB-041 are pooled, neutralized with a 32% aqueous ammonia solution and concentrated under vacuum.

The solution obtained in this manner is fed over silica in C18 reverse phase and eluted with water.

The fractions containing the antibiotic AB-041 are pooled, concentrated under vacuum and fed through a size exclusion chromatography column containing for example FRAKTOGEL TSK HW40(F) as stationary phase, and eluted with water, the fractions containing the antibiotic AB-041 are pooled and concentrated under vacuum to provide the pure antibiotic AB-041.

Biological activity

The herbicidal activity both before and after emergence was determined by the methods reported in the examples.

The compound AB-041 has considerable post-emergence herbicidal activity on a wide range of monocotyledon and dicotyledon infesting grasses of different botanical groups (see Table E). The pre-emergence herbicidal activity is however limited to certain dicotyledon species (see Table E, below).

The compound AB041 also shows selectivity towards certain species of useful plants such as wheat, barley, maize and cotton (see Table F below, these being little phytotoxic at the doses active against the infesting grasses.

The properties demonstrated show that the antibiotic of our invention possesses phytotoxic activity of agricultural interest and can therefore be usefully applied as a herbicide.

Use and formulation

In practice, both in agriculture and in other sectors of application, the compound of the invention is most usefully used in the form of suitable compositions.

In addition to the active principle, these compositions contain solid or liquid inert carriers (organic solvents, vegetable or mineral oils, water and their mixtures) and possibly other additives normally used in formulations such as surfactants, dispersants and wetting agents.

For example, in view of its positive characteristics in terms of solubility and stability in water, the product can be conveniently formulated as a water-soluble powder or aqueous solution to minimize the environmental impact deriving from the use of organic solvents.

The methods of application are chosen in relation both to the objectives to be attained and to the type of formulation to be used.

For particular applications or to extend the range of action of the compositions, other active ingredients such as other herbicides, insecticides, fungicides or fertilizers can be added to the aforesaid compositions.

The applied doses vary according to different factors, such as the type and degree of infestation, the type of composition used, and climatic and environmental factors.

For practical uses in agriculture, antibiotic doses of between 0.1 and 2 kg/ha give satisfactory results.

The following examples illustrate the invention but without being limitative thereof.

EXAMPLE 1

Test of post-emergent herbicidal activity

Seeds of ten varieties of infesting grass annuals pertaining to different botanical groups were sown in plastic jars of 11 cm diameter containing agricultural earth and made to grow under suitable conditions in a greenhouse for 7-15 days depending on the species, until the cotyledon leaves had expanded in the case of the dicotyledon species, and until the first leaf had extended and the second was visible in the case of the monocotyledon species. A 1.0 g/l aqueous solution of AB-041 (corresponding to a dose of 1.0 kg/ha) is administered to the plants under test by a De Vilbiss atomizer. The herbicidal effect is noted weekly. Table E shows the activity results after four weeks, expressed as a percentage of growth inhibition. All the plants of the varieties under test show inhibition levels of between 60% and 100% (0%=healthy plant; 100%=completely inhibited plant).

EXAMPLE 2

Test of pre-emergent herbicidal activity

Seeds of ten varieties of infesting grass annuals pertaining to different botanical groups were sown in plastic jars of 11 cm diameter containing agricultural earth. A 1 g/l aqueous solution of AB-041 (corresponding to a dose of 1 kg/ha) is administered to the surface of the earth contained in the jars by a De Vilbiss atomizer. The herbicidal effect is noted weekly.

Table E shows the activity results after four weeks, expressed as a percentage of growth inhibition (0%=healthy plant; 100%=completely inhibited plant).

TABLE E

| INFESTING PLANT | AB-041 1 kg/ha % growth inhibition | |
|---|---|---|
| | post-emergence | pre-emergence |
| Convolvolus arvensis | 75 | 70 |
| Convolvolus sepium | 100 | 90 |
| Ipomea leptofilla | 85 | 35 |
| Geranium dissectum | 95 | 0 |
| Stellaria media | 100 | 100 |
| Abutilon theophrasti | 100 | 10 |
| Solanum nigrum | 95 | 20 |
| Veronica sp. | 100 | 20 |
| Setaria glauca | 60 | 10 |
| Digitaria sanguinalis | 75 | 10 |

EXAMPLE 3

Test of post-emergent herbicidal activity on useful plants The test is conducted as described in the paragraph "Post-emergent herbicidal activity" on six useful monocotyledon and dicotyledon plants.

Table F shows the activity results after four weeks, expressed as a percentage of growth inhibition.

TABLE F

| CROP | AB-041 1 kg/ha % growth inhibition |
|---|---|
| Triticum aestivum | 5 |
| Hordeum vulgare | 0 |
| Zea mays | 15 |
| Glycine maxima | 15 |
| Beta vulgaris | 55 |
| Pisum sativum | 70 |
| Gossypium hirsutum | 0 |

The species showing no sign of phytotoxicity are cotton (*Gossypium hirsutum*) and barley (*Hordeum vulgate*). Wheat (*Triticum aestivum*), maize (*Zea Mays*) and soya (*Glycine maxima*) show small signs of phytotoxicity of between 5% and 15%.

Beet (*Beta vulgaris*) and pea (*Pisum sativum*) are the most sensitive species, showing growth inhibition of 55% and 70% respectively.

EXAMPLE 4

Fermentation of the Streptomyces sp. NCIMB 40428 strain

A vial containing 2 ml of Streptomyces NCIMB 40428 mycelium (preserved in 10% glycerol at −20° C.) is used to inoculate 150 ml of the aforesaid culture medium V, this being then incubated in a rotary shaker (150 rpm) at 28° C. for 72 hours.

The culture obtained is used to inoculate a fermenter (nominal volume 10 l) containing 7 l of culture medium P plus 1.0 g/l of Nixolen as antifoaming agent, under the following conditions: temperature 29° C., aeration 300 l/h, agitation 320 rpm, duration of fermentation about 96 hours.

EXAMPLE 5

Fermentation of the Streptomyces sp. NCIMB 40428 strain

A vial containing the strain Streptomyces sp. NCIMB 40428 in lyophilized form is open asceptically and rehydrated with sterile distilled water. The suspension is used to inoculate a 500 ml flask containing 100 ml of the aforedescribed culture medium P, this being then incubated for 90 hours at 28° C. in a rotary shaker(200 rpm). At the end of this period the culture broth is centrifuged to separate it from the mycelium and is used for biological tests.

EXAMPLE 6

Fermentation of the Streptomyces sp. NCIMB 40428 strain

A pure culture of Streptomyces sp. NCIMB 40428 grown on the culture medium S is used to inoculate three flasks each containing 20 ml of culture medium V, which are then incubated at 28° C. in a rotary shaker (250 rpm) for 72 hours.

The cultures are used to inoculate ten 2.0 l flasks each containing 500 ml of culture medium V1, which are again incubated under the aforesaid conditions for 72 hours.

At the end of this period the culture is used to inoculate three fermenters (nominal volume 40 l) containing 25 1 of culture medium P plus 1.0 g/1 of Nixolen as antifoaming agent, under the following conditions: temperature 29° C., aeration 300 1/hour, duration of fermentation 74 hours.

EXAMPLE 7

Isolation of the antibiotic AB-041

90 liters of fermentation broth obtained in the aforesaid manner are centrifuged and the clarified broth is filtered through a 1 μm filter.

The filtrate is treated in an ultrafiltration/reverse osmosis unit (Hydro Air Research S.R.L., Zerbo di Opera, Italy) fitted with a G-50 spiral membrane with 20 kD nominal exclusion (Hydro Air Research).

About 80 liters are allowed to permeate, after which 10 liters of water are added to the retained liquid and a further 10 liters are allowed to permeate, these being added to the 80 liters of permeate previously obtained.

The matter retained by the ultrafiltration is discarded.

The 90 liters of the ultrafiltration permeate are treated in a reverse osmosis unit (Hydro Air Research) fitted with a DS-5 reverse osmosis spiral membrane with 500D nominal exclusion (Hydro Air Research).

82 liters are allowed to permeate and the concentrate collected, the module is washed with 2.5 liters of water and the wash water added to the reverse osmosis concentrate to obtain 9.5 liters of solution containing the antibiotic AB-041.

This is fed into a column (internal diameter 90 mm×300 mm height) containing 2.4 kg of XAD-4 (Rohm & Haas Co., Philadelphia, Pa.), to collect 8.0 1 of eluate.

The resin is washed with 4.0 1 of water, collecting the first 1.5 liters, which are added to the previous 8.0 1 of eluate. This solution, with a pH of about 7.1 and containing the antibiotic AB-041, is fed at a rate of 20 ml/min into a column (internal diameter 90 mm×300 mm height) containing 1.5 kg of Amberlite IRA 401, 20-50 mesh (Fluka Chemic AG, Buchs, Switzerland) in chloride form, the column then being washed with 6.0 liters of water and eluted with a 0.5N aqueous HCl solution. The antibiotic AB-041 is eluted within 7 liters after 4 liters of eluent.

The acid solution containing the antibiotic AB-041 is neutralized with a 32% aqueous ammonia solution, is concentrated under vacuum to a volume of about 1.0 liter and is fed into a column (internal diameter 90 mm×500 mm height) containing 1.2 kg of RSiL C18 HL silica (0.044–0.063 mm, porosity 90 A: Bio-Rad Laboratories S.r.l. Milan, Italy) and eluted at a rate of 35 ml/min with water.

The antibiotic AB-041 is eluted within 3.2 liters after 7.5 liters of eluent. This quantity is evaporated to dryness under vacuum, taken up in 50 ml of water, fed into a column (internal diameter 70 mm×500 mm height) filled with FRAKTOGEL TSK HW 40(F) (Merck AG. Darmstadt, Germany) and eluted with water at a rate of 5 ml/min, 35 ml fractions being collected.

The antibiotic AB-041 is eluted within 350 ml from fraction 21 to fraction 30.

The collected fractions are evaporated under vacuum to obtain 300 mg of the antibiotic AB-041.

EXAMPLE 8

| Formulation: preparation of a water-soluble powder | |
| --- | --- |
| a) active principle (AB-041) | 70–90% |
| b) calcium ligno sulphonate | 2–5% |
| c) anionic or non-ionic surfactant (sodium benzenesulphonate, condensed naphthalene-formaldehyde, polyethoxylated alkylphenols etc., either alone or in mixture) | 5–10% |
| d) silicone antifoaming agent | 0.5–2% |
| possibly plus inert soluble salts such as sodium sulphate, KCl etc. | |

EXAMPLE 9

| Formulation: preparation of a concentrated aqueous solution | |
| --- | --- |
| a) active principle (AB-041) | 5–15% |
| b) polyethoxylated nonylphenol | 1–5% |
| c) propyleneglycol | 5–10% |
| d) polyethoxylated alkylamine | 2–5% |
| e) water to make up to 100% | |

We claim:

1. An AB-041 antibiotic, produced by Streptomyces sp. NCIMB 40428 or a mutant equivalent thereof during controlled aerobic cultivation in an aqueous culture medium containing carbon, nitrogen and inorganic salt sources; said antibiotic having:

an ultraviolet absorption maximum at 278 nm, infrared absorption maxima ($cm^{-1}$) at 3395, 1663, 1594, 1449, 1403, 1338, 1307, 1285, 1246, 1225, 1159, 1102, 1074, 1037, 1017, 960, 942, 917, 888 and 741, and an empirical formula of $C_{16}H_{25}N_5O_9S$.

2. The AB-041 antibiotic of claim 1, said antibiotic further having good solubility in water, dimethylsulphoxide and mixtures thereof, but being practically insoluble in ethyl ether and hexane.

3. The AB-041 antibiotic of claim 2, said antibiotic further having an $^{-1}HNMR$ spectrum having principal peaks, relative to TMS, at (ppm): 8.26 (s, 1H), 4.55 (t, 1H), 4.43 (d, 1H), 4.26 (d, 1H), 4.04 (m, 1H), 3.67 (m, 3H), 3.36 (t, 1H), 3.26 (t, 1H), 3.09 (m, 1H), 2.71 (dd, 1H), 2.19 (d, 1H) and 1.26 (d, 3H).

4. The AB-041 antibiotic of claim 3, said antibiotic further having a $^{13}CNMR$ spectrum having principal peaks, relative to TMS, at (ppm): 181.3 (s), 174.7 (s), 165.8 (s), 158.3 (s), 137.8 (s), 107.8 (s), 105.3 (s, very weak), 73.1 (d), 66.8 (t), 62.0 (t), 51.1 (d), 47.3 (t), 43.6 (d), 43.6 (t), 42.0 (d) and 18.5 (q).

5. An antibiotic AB-041, having the following properties:

(a) good solubility in water, in dimethylsulphoxide and dimethylsulphoxide/water mixtures, but practically insoluble in ethyl ether and hexane;

(b) by elemental analysis, contains carbon, hydrogen, nitrogen, oxygen and sulphur;

(c) a molecular weight of 463 g/mol;

(d) an ultraviolet absorption maximum at 278 nm;

(e) infrared absorption maxima at 3395, 1663, 1594, 1449, 1403, 1338, 1307, 1285, 1246, 1225, 1159, 1102, 1074, 1037, 1017, 960, 942, 917, 888 and 741 $cm^{-1}$;

(f) an $^1HNMR$ spectrum having principal peaks, relative to TMS, at (ppm): 8.26 (s, 1H), 4.55 (t, 1H), 4.43 (d, 1H), 4.26 (d, 1H), 4.04 (m, 1H), 3.67 (m, 3H), 3.36 (t, 1H), 3.26 (t, 1H), 3.09 (m, 1H), 2.71 (dd, 1H), 2.19 (d, 1H) and 1.26 (d, 3H);

(g) a $^{13}$CNMR spectrum having principal peaks, relative to TMS, at (ppm): 181.3 (s), 174.7 (s), 165.8 (s), 158.3 (s), 137.8 (s), 107.8 (s), 105.3 (s, very weak), 73.1 (d), 66.8 (t), 62.0 (t), 51.1 (d), 47.3 (t), 43.6 (d), 43.6 t), 42.0 (d) and 18.5 (q);

(h) a positive colorimetric reaction with ninhydrin in acetone (0.2% w/v) and with pinacryptol yellow in water (0.07% w/v), and a negative colorimetric reaction with a diazotization reagent and coupling with α-naphthol; and (i) a retention factor (Rf) of 0.35 on a cellulose F chromatography plate with 91:9 acetonitrile/water (v/v) as eluent.

6. A method of inhibiting the growth of a plant, comprising applying an herbicidally effective amount of the antibiotic of claim 1 to a plant or earth in need thereof.

7. The method of claim 6, wherein said effective amount is between 0.1 and 2 kg/ha.

8. The method of claim 6, wherein said plant is grass, and said antibiotic is applied to said grass after the emergence of said grass.

9. The method of claim 6, wherein said antibiotic is applied before the emergence of said plant.

10. The method of claim 6, wherein said antibiotic is applied, as an aqueous solution.

11. The method of claim 6, wherein said plant is selected from the group consisting of *Convolvolus arvensis, Convolvolus sepium, Ipomea leptofilla, Geranium dissectum, Stellaria media, Abutilon theophrasti, Solanum nigrum,* Veronica sp., *Setaria glauca* and *Digitaria sanguinalis.*

12. The method of claim 6, wherein said plant is *Convolvolus arvensis, Convolvolus sepium* or *Stellaria media.*

13. An herbicidal composition containing an herbicidally effective amount of an antibiotic of claim 1, and a solid or liquid inert carrier.

14. The composition of claim 13, furthering comprising a surfactant, dispersant, wetting agent, or mixture thereof.

15. The composition of claim 13, wherein said inert carrier is water.

16. The composition of claim 14, further comprising an insecticide, a fungicide, or a fertilizer.

17. The method of claim 12, wherein said antibiotic is applied before the emergence of said plant.

18. The micro-organism Streptomyces sp. NCIMB 40428.

19. A biological pure culture of the microorganism Streptomyces sp. NCIMB 40428, which produces the AB-041 antibiotic of claim 1.

* * * * *